United States Patent [19]
Ozbalik

[11] Patent Number: 5,146,000
[45] Date of Patent: Sep. 8, 1992

[54] PRODUCTION OF DIHYDROCARBYL POLYSULFIDES

[75] Inventor: Nubar Ozbalik, Baton Rouge, La.

[73] Assignee: Ethyl Corporation, Richmond, Va.

[21] Appl. No.: 674,148

[22] Filed: Mar. 25, 1991

[51] Int. Cl.$^5$ ............................................ C07C 321/20
[52] U.S. Cl. ......................................... 568/26; 568/25
[58] Field of Search .................................. 568/26, 25

[56] References Cited

U.S. PATENT DOCUMENTS

| | | | |
|---|---|---|---|
| 2,237,625 | 4/1941 | Olin | 260/125 |
| 2,558,221 | 6/1951 | Mertz et al. | 260/608 |
| 2,574,884 | 11/1951 | Mertz et al. | 260/608 |
| 3,022,351 | 2/1962 | Mihan et al. | 260/608 |
| 3,275,693 | 9/1966 | Bapseres et al. | 260/608 |
| 3,308,166 | 3/1967 | Biensan et al. | 260/608 |
| 3,340,324 | 9/1967 | Warner | 260/608 |
| 3,392,201 | 7/1968 | Warner | 260/608 |
| 3,452,100 | 6/1969 | Bennet et al. | 260/608 |
| 3,994,979 | 11/1976 | Warner | 568/26 |
| 4,277,623 | 7/1981 | Kubicek | 260/608 |
| 4,288,627 | 9/1981 | Kubicek | 568/26 |
| 4,564,709 | 1/1986 | Koyama et al. | 568/26 |
| 4,876,389 | 10/1989 | Gongora et al. | 568/26 |
| 4,933,481 | 6/1990 | Vallee et al. | 568/26 |
| 4,937,385 | 6/1990 | Buchholz et al. | 568/26 |

FOREIGN PATENT DOCUMENTS

| | | | |
|---|---|---|---|
| 839767 | 4/1970 | Canada | 260/609 |
| 885990 | 11/1971 | Canada | 253/97 |
| 0025944 | 9/1980 | European Pat. Off. | 149/12 |
| 0337837 | 8/1990 | France | 319/14 |
| 8140063 | 8/1983 | Japan | 149/12 |
| 59-10559 | 1/1984 | Japan | 149/12 |
| 1160473 | 6/1967 | United Kingdom | 149/12 |

*Primary Examiner*—Marianne M. Cintins
*Assistant Examiner*—John Peabody
*Attorney, Agent, or Firm*—David E. LaRose

[57] ABSTRACT

Hydrocarbyl mercaptan is reacted with sulfur in the presence of added alumina catalyst. With tertiary alkyl mercaptans high yields of di-tert-alkyl trisulfides are formed with excellent selectivity. With primary alkyl mercaptans the process can be controlled to form products enriched in either dialkyl disulfides or dialkyl trisulfides, and in either case little or no tetrasulfides are formed. The process is environmentally friendly in that halogen-containing reactants such as sulfur chlorides are not used and thus the products are not contaminated with significant amounts of halogen residues.

23 Claims, No Drawings

PRODUCTION OF DIHYDROCARBYL POLYSULFIDES

This invention relates to a process for production of dihydrocarbyl polysulfides, and more particularly to a process for selective synthesis of dihydrocarbyl trisulfides.

Prior methods for production of dihydrocarbyl polysulfides, such as dialkyl polysulfides, based on use of mercaptans and sulfur as raw materials are described for example in U.S. Pat. Nos. 2,237,625, 3,022,351, 3,275,693, 3,308,166, 3,314,999, 3,340,324, 3,392,201, 3,452,100, 3,755,461, 3,994,979, 4,564,709, 4,876,389, 4,933,481, and 4,937,385; British Pat. Spec. No. 1,160,473; Canadian Pat. Nos. 839,767 and 885,990; European Pat. App. Pub. No. 25,944 and 337,837; and Japan Kokai (Laid-Open application) Nos. 58-140,063 and 59-10559.

Another prior approach for producing dihydrocarbyl polysulfides involves oxidizing a mercaptan with air or free oxygen in the presence of a catalyst. In U.S. Pat. No. 2,558,221 the catalyst is a selected natural bauxite which contains on a weight basis 50–70% $Al_2O_3$, 8–20% $Fe_2O_3$, 2–8% $SiO_2$, 0.5–5% $TiO_2$, and 2–30% volatile matter as determined by ignition at 1800° F. In U.S. Pat. No. 2,574,884 the catalyst is alumina associated with a minor amount of vanadia, magnetic iron oxide or chromia. In U.S. Pat. No. 4,277,623 a catalyst system comprising a cobalt molybdate-alkali metal and/or alkaline earth metal hydroxide is used as the oxidation catalyst. And in U.S. Pat. No. 4,288,627 the oxidation catalyst is a supported cobalt molybdate catalyst used in combination with a liquid tertiary amine.

It is also known that dihydrocarbyl polysulfides can be formed by reacting mercaptans with sulfur chlorides such as sulfur monochloride and sulfur dichloride.

Of the various dihydrocarbyl polysulfides, dihydrocarbyl trisulfides are particularly desirable for use as antiwear and extreme pressure lubricant additives because of their superior performance capabilities and their generally lower corrosiveness towards "yellow metals" such as copper. Thus one object of this invention is to provide a new and efficient method for selectively producing dihydrocarbyl trisulfides—i.e., a method for producing dihydrocarbyl polysulfides enriched in dihydrocarbyl trisulfide content.

Processes are known whereby dihydrocarbyl polysulfides containing a substantial proportion of dihydrocarbyl tetrasulfides, dihydrocarbyl pentasulfides and the like can be converted to a product enriched in dihydrocarbyl trisulfide. Thus another object of this invention is to provide a process for producing dihydrocarbyl polysulfides of the formula, $R-S_x-R$, where R is hydrocarbyl and x is an integer representing the average number of sulfur atoms in the product and is above 3.0, e.g., at least 3.2, and preferably is in the range of about 3.5 to 4.0.

This invention provides an economical process for preparing dihydrocarbyl polysulfides from hydrocarbyl mercaptans in high yields. Typically, this invention enables high yield synthesis of dihydrocarbyl polysulfides, especially tertiary hydrocarbyl polysulfides, wherein the average number of sulfur atoms in the product (usually a product mixture) is in the range of about 3 to about 4. Primary hydrocarbyl polysulfides wherein the average number of sulfur atoms in the product is in the range of about 2 to about 3 can also be formed by the process of this invention. Products of this type are also of known utility in the chemical and allied arts. In one of its preferred forms, this invention provides a process enabling selective conversion of hydrocarbyl mercaptans to dihydrocarbyl trisulfides in high yields. In another of its preferred forms a process is provided in which reaction rate is high, reaction time can be short, and dihydrocarbyl trisulfides can be formed with high selectivity and in high yields.

In accordance with this invention, a hydrocarbyl mercaptan, is reacted with sulfur using an alumina catalyst, preferably an activated alumina catalyst, and most preferably an activated neutral alumina of particle size within the range of 80–200 mesh. In a preferred embodiment, the alumina-catalyst is employed in amount such that the alumina:mercaptan mole ratio is at least about 0.01 and more preferably is at least about 0.03, as this results in a rapid, yet highly selective, high-yield reaction.

In another embodiment, the alumina catalyst is recycled from one run to the next. This procedure can be repeated, while augmenting the catalyst with fresh catalyst if necessary or desired, so long as the catalyst remains catalytically active in the process. When conducting the process with the objective in mind of forming dihydrocarbyl trisulfide with high selectivity, it is desirable to employ fresh catalyst or recycled catalyst which has not lost its ability to provide a product enriched in the trisulfide product. The number of times a given quantity of catalyst can be reused will depend on the characteristics of the particular catalyst selected for use and the particular reaction conditions under which it is used, but can be readily determined by the simple expedient of performing a few trial experiments in which the selected catalyst is recycled in a series of runs conducted under a selected set of reaction conditions.

It will be noted that this invention forms dihydrocarbyl polysulfide products that are not contaminated with significant quantities of contained halogen, as is often the case when using sulfur chlorides as the sulfur source. Thus the process of this invention is of particular advantage from the environmental standpoint.

Mercaptans which may be used in the process include compounds of the formula RSH where R is alkyl, alkenyl, alkynyl, cycloalkyl, cycloalkylalkyl, aryl, aralkyl, alkaryl, cycloalkylaryl, cycloalkenyl, and like hydrocarbyl groups. There is no known restriction or limitation on the number of carbon atoms that can be present in the hydrocarbyl group. Thus it is contemplated that the process can be used with mercaptans having perhaps 1000 or more carbon atoms in the molecule, although in most cases they will contain 100 carbon atoms or less. Preferred are alkyl mercaptans, most preferably tertiary alkyl mercaptans, having up to about 24 carbon atoms, with use of tert-butyl mercaptan (2-methyl-2-propanethiol) being particularly preferred.

The sulfur used is preferably either precipitated sulfur or flowers of sulfur. However, use can be made of any form of sulfur that is co-reactive with the mercaptan being used. Although powdered forms of sulfur are generally employed, it is possible to use molten sulfur.

As noted above, an alumina catalyst is used in the process, i.e., alumina is charged into the reaction vessel. It is not known what catalyst transformations, if any, take place in situ during the reaction, and thus the identity of the actual catalytic species responsible for the reaction enhancement brought about by use of alumina is not known. It has been observed, however, that after repeated use in an extended series of reaction, the rate of dihydrocarbyl trisulfide formation tends to decrease. This would suggest that a portion of the catalyst may be deactivated during the reaction. Whatever its form and/or composition, this invention involves the use of any suitably active alumina catalyst in the process.

The relative proportions of sulfur and mercaptan can be varied within relatively wide limits (e.g., from about 1.5:1.0 to about 0.3:1.0 gram atoms of sulfur per mol of hydrocarbyl mercaptan) to produce a wide variety of dihydrocarbyl polysulfides. In general, the higher the ratio of sulfur to mercaptan, the higher the sulfur content of the dihydrocarbyl polysulfide product, typically up to a ceiling of about $R-S_{3.7}-R$. When it is desired to form dihydrocarbyl trisulfide with high selectivity, a ratio of about 1.0 to about 0.5 gram atoms of sulfur per mol of mercaptan should be used.

Reaction temperatures are typically in the range of about 25° to about 150° C., preferably in the range of about 25° C. to about 110° C. and more preferably in the range of about 60° to about 90° C. Reaction times generally fall in the range of about 0.5 to about 5 hours, and preferably are in the range of about 1 to about 2 hours. The reaction mixture should be stirred or subjected to other forms of physical agitation in order to insure intimate contact among the reactants and catalyst.

Among the various embodiments of this invention is a process as described above wherein the hydrocarbyl mercaptan is an alkyl mercaptan, wherein the alumina catalyst is in particulate form as charged to the reaction vessel, and wherein the reaction temperature is within the range of 25° to about 150° C.

Another embodiment involves forming a mixture from at least one liquid alkyl mercaptan, sulfur and a catalytically active form of alumina, and applying heat and agitation to such mixture such that dialkyl polysulfide is formed. As in all embodiments of this invention, the reaction can be conducted with or without the inclusion in the reaction mixture of a suitable liquid diluent such as a liquid hydrocarbon. Preferably the reaction mixture contains from about 0.3 to about 1.5 gram atoms of sulfur per gram mol of the liquid alkyl mercaptan. Reaction temperatures in this embodiment are desirably in the range of about 40° to about 150° C., and the reaction mixture preferably contains about 0.005 to about 0.05 gram mol of alumina catalyst per gram mol of mercaptan charged to the reaction mixture.

When using tert-alkyl mercaptans in the process of this invention, temperatures within the range of about 25° to about 150° C. are suitable, with temperatures in the range of about 60° to about 80° C. being preferred. Here again the reaction mixture preferably contains from about 0.3 to about 1.5 gram atoms of sulfur per gram mol of tert-alkyl mercaptan charged to the system, and the reaction mixture desirably contains about 0.005 to about 0.05 gram mol of alumina catalyst per gram mol of mercaptan introduced into the reaction mixture. As noted above, the alumina is preferably in particulate form, and the reaction can be conducted in bulk or in the presence of ancillary liquid diluent. More preferred forms of alumina catalyst are activated alumina in particulate form, such as a neutral activated alumina of about 80 to about 200 mesh size.

Example 1 illustrates a use of an alumina catalyst pursuant to this invention.

EXAMPLE 1

150 mL (1.33 mol) of tert-butyl mercaptan was added to a solid mixture of 21.3 g (0.67 g-at) of sulfur and 2.41 g (0.023 mol) of alumina catalyst. The mixture was stirred vigorously at reflux (75° C.) for 1 hour. The catalyst was filtered off and the filtrate was concentrated under reduced pressure at 80° C. until removal of excess mercaptan was complete (69 mL). The residue was then vacuum stripped about 140° C. to yield 66.9 g (95.6% based on sulfur) of colorless odor-free oil. The gas chromatogram of the product showed 0.5% di-tert-butyl-disulfide, 96.2% trisulfide and 2.9% tetrasulfide.

Example 2 illustrates the effect of the ratio of sulfur to mercaptan in the synthesis of tert-butyl polysulfide.

EXAMPLE 2

Four runs were performed in which 100 mL (0.887 mol) of tert-butyl mercaptan and 2.41 (0.0234 mol) of alumina were refluxed with varied amounts of sulfur for 2.5 hours. The reaction mixtures were then filtered and analyzed by gas chromatography. The results are given in Table 1.

TABLE 1

| Run | Mole Ratio S:RSH | GC Percentage S2 | S3 | S4 | S > 4 | Average No. Sulfur atoms |
|---|---|---|---|---|---|---|
| 1 | 1.5 | 0.4 | 36.9 | 54.1 | 8.5 | ca. 3.70 |
| 2 | 1.0 | 0.2 | 75.6 | 23.5 | trace | 3.21 |
| 3 | 0.8 | 0.9 | 88.0 | 10.2 | — | 0.07 |
| 4 | 0.6 | 1.4 | 94.6 | 3.2 | — | 2.97 |

Example 3 serves to illustrate the use and effect of catalyst recycle in the synthesis of tert-butyl polysulfide.

EXAMPLE 3

Alumina was recycled through six consecutive runs in which solid filtered from a run was used as a catalyst in the next run. In each case, the concentration of catalyst (25.2 mg/mL) and mol ratio of tert-butyl mercaptan (0.444 mol) to sulfur (1.0:0.6) were kept constant. All the runs were conducted at 70° C. for 55 min, except for the last one in which the reaction time was extended to 18 hours. Samples taken in the course of the reactions were analyzed. The results are summarized in Table 2 wherein yield is calculated based on the equations $2RSH + 2S \rightarrow R_2S_3 + H_2S$ and $2RSH + 3S \rightarrow R_2S_4 + H_2S$ which render sulfur as the limiting reagent.

TABLE 2

| Run | | GC Percentage S2 | S3 | S4 | g. Product | % Yield |
|---|---|---|---|---|---|---|
| 1 | | 0.47 | 94.7 | 4.26 | 23.2 | 83.2 |
| 2 | | 0.28 | 92.8 | 6.25 | 25.8 | 93.4 |
| 3 | | 0.24 | 89.1 | 9.83 | 25.6 | 94.2 |
| 4 | | 0.24 | 83.7 | 15.0 | 25.7 | 94.2 |
| 5 | | 0.17 | 56.9 | 41.2 | 23.4 | 93.2 |
| 6 | 60 min | — | 65.4 | 34.6 | | |
| | 140 min | 1.87 | 89.9 | 8.20 | | |
| | 18 hrs | 8.18 | 86.6 | 5.19 | | |

Example 4 further illustrates the effect of the ratio of sulfur to mercaptan in the synthesis of tert-butyl polysulfide.

EXAMPLE 4

Three runs were conducted in which 150 mL (1.33 mol) of tert-butyl mercaptan and 2.41 g (0.0234 mol) of alumina were refluxed with varied amounts of sulfur for one hour. Samples of the products were tested for copper corrosiveness according to ASTM D-130 modified by use of a temperature of 121° C. rather than the customary 100° C. temperature. The results of these runs and tests are summarized in Table 3 wherein the yield is calculated based on the equation $2RSH + 2S \rightarrow R_2S_3 + H_2S$ which renders sulfur as the limiting reagent in these runs, and wherein CCT refers to the amount of copper corrosion in the D-130 test.

TABLE 3

| Run | Mol Ratio, S:RSH | GC Percentages S2 | S3 | S4 | CCT | % Yield | Mass Balance |
|---|---|---|---|---|---|---|---|
| 1 | 0.5 | 0.54 | 96.2 | 2.9 | 4.4 | 95.6 | 94 |
| 2 | 0.4 | 0.58 | 97.1 | 1.8 | 27.1 | 100 | 95 |
| 3 | 0.3 | 1.21 | 97.7 | 0.72 | 19.8 | 96.5 | 97 |

Example 5 illustrates the effect of temperature in the synthesis of di-tert-butyl polysulfides pursuant to this invention.

EXAMPLE 5

Three runs were conducted using 25. o mL (0.222 mol) of tert-butyl mercaptan, 3.55 g (0.111 gram atoms) of sulfur and 0.504 g of alumina catalyst. The respective reactions were conducted at 25° C., 50° C., and 75° C. Samples of the reaction mixture were taken at different time intervals and subjected to gas chromatographic analysis to determine product composition. The results are summarized in Table 4.

TABLE 4

| Run | Temp., °C. | Time, hr. | GC Percentages S2 | S3 | S4 | Unknown |
|---|---|---|---|---|---|---|
| 1 | 25 | 1.0 | 0.21 | 6.6 | 89.4 | 3.6 |
|   |    | 1.5 | 0.22 | 13.5 | 82.0 | 4.0 |
|   |    | 1.8 | 0.32 | 37.4 | 59.1 | 3.0 |
| 2 | 50 | 1.0 | 0 | 37.0 | 60.3 | 2.7 |
|   |    | 1.7 | 0 | 58.1 | 40.0 | 2.0 |
|   |    | 3.0 | 0 | 67.3 | 30.7 | 1.8 |
| 3 | 75 | 1.0 | 0.6 | 96.2 | 2.74 | 0.4 |

It was subsequently found that the "unknown" in the above table was 2-methyl-2-propanesulfenothioic acid (RSSH).

EXAMPLE 6

A number of runs were carries out in which various alkyl mercaptans were sulfurized in the presence of alumina. In runs 1 to 6, the mol ratio of mercaptan to sulfur was 1.0:0.5. In runs 7 and 8 the respective mercaptan to sulfur mol ratios were 1.0 to 1.2 and 1.0 to 1.5. The reaction conditions and the gas chromatography results are summarized in Table 5 wherein the tr represents "trace".

TABLE 5

| Run | RSH (mL) | Reaction Conditions Temp (°C.) | Time (hr) | GC Percentage S2 | S3 | S4 |
|---|---|---|---|---|---|---|
| 1 | t-butyl (150) | 70-75 | 1.0 | 0.6 | 96 | 2.7 |
| 2 | t-nonyl (25) | 80-85 | 18 | 10 | 86 | 1.7 |
| 3 | t-dodecyl (200) | 75 | 3.0 |  |  |  |
|   |   | 100-105 | 2.5 |  |  |  |
| 4 | n-butyl (200) | 70 | 1.0 | 81 | 17 |  |
| 5 | n-nonyl (5.0) | 75-80 | 1.0 | 83 | 17 |  |
| 6 | n-octyl (25) | 80 | 1.0 | 86 | 14 |  |
| 7 | n-octyl (25) | 85 | 1.5 | 39 | 61 | tr |
| 8 | n-octyl (25) | 90 | 1.0 | 31 | 69 | tr |

EXAMPLE 7

A group of reactions were carried out in which 100 mL of tert-butyl mercaptan was reacted with 25.5 g of sulfur in the presence of various quantities of alumina at 75°-80° C. The amounts of catalyst used in the respective runs and the results thereof are summarized in Table 6.

TABLE 6

| Run | Catalyst amt., g | Time, min. | GC Percentage S2 | S3 | S4 | RSSH |
|---|---|---|---|---|---|---|
| 1 | 4.8 | 30 | 0.22 | 79.9 | 18.9 | 0.61 |
|   |    | 60 | 0.33 | 82.5 | 16.4 | 0.46 |
| 2 | 2.4 | 60 | 0.26 | 81.4 | 17.4 | 0.55 |
|   |    | 110 | 0.48 | 82.4 | 16.5 | 0.46 |
| 3 | 1.2 | 60 | 0.06 | 69.6 | 29.3 | 0.88 |
|   |    | 110 | 0.12 | 80.1 | 18.7 | 0.62 |
|   |    | 150 | 0.16 | 81.7 | 17.5 | 0.50 |
| 4 | 0.6 | 68 | 0.21 | 45.7 | 52.5 | 1.39 |
|   |    | 110 | 0.18 | 66.8 | 31.8 | 0.87 |
|   |    | 150 | 0.21 | 76.6 | 22.2 | 0.70 |
|   |    | 210 | 0.22 | 79.2 | 19.8 | 0.60 |
| 5 | 0.3 | 70 | 0.20 | 17.6 | 79.5 | 2.21 |
|   |    | 110 | 0 | 23.7 | 74.3 | 1.76 |
|   |    | 150 | 0 | 35.6 | 62.7 | 1.50 |
|   |    | 330 | 0.15 | 63.1 | 35.7 | 0.94 |

EXAMPLE 8

A series of runs were conducted using a number of different forms of commercially available alumina in order to determine activity in the process. In each case, the reaction mixture was composed of tert-butyl mercaptan and sulfur in a mol ratio of 1:0.9. It was found that an activated chromatographic grade of 80-200 mesh size from EM Science was the most active of those tested. Other useful grades were (a) activated, basic, Brockmann I, standard grade, 150 mesh, 58 angstroms, surface area: 155 m$^2$/g, from Aldrich Chemical; (b) activated, acidic, Brockmann I, standard grade, 150 mesh. 58 angstroms, surface area: 155 m$^2$/g, from Aldrich Chemical; (c) gamma alumina, 99.99%, 0.01 micron, from Johnson Matthey; and (d) activated, granular alumina, 99%, from Johnson Matthey. It was also found that a fused alumina of $-325$ mesh size and a calcined alumina of $-100$ to 200 mesh size were inactive in the process.

It will be seen from the foregoing examples that with tertiary hydrocarbyl mercaptans such as tertiary alkyl mercaptans having 4 to 12 or more carbon atoms, tertiary hydrocarbyl mercaptans can be formed in high yields and with excellent selectivity. It will also be noted that with primary hydrocarbyl mercaptans the process can be controlled to form products enriched in either dihydrocarbyl disulfides or dihydrocarbyl trisulfides, and in either case little or no tetrasulfides are formed. See in this connection, Runs 4-8 of Example 6.

This invention is susceptible of considerable variation in its practice. Thus this invention is not intended to be limited to the specific exemplifications set forth hereinabove. Rather what is intended to be covered is subject matter within the spirit and scope of the appended claims and equivalents thereof.

What is claimed is:

1. A process for forming a mixture of dihydrocarbyl polysulfides which comprises reacting hydrocarbyl mercaptan with sulfur in the presence of added alumina catalyst at a temperature and for a period of time which are sufficient to form said dihydrocarbyl polysulfide, wherein said temperature is about 25° C. to about 110° C.

2. A process as claimed in claim 1 wherein the hydrocarbyl mercaptan is an alkyl mercaptan and wherein the alumina catalyst is in particulate form.

3. A process for producing dialkyl polysulfide which comprises forming a mixture from at least one liquid alkyl mercaptan, sulfur and catalytically active form of alumina, heating said mixture to one or more temperatures of about 25° C. to about 110° C. and agitating said heated mixture for a period of time sufficient to form said dialkyl polysulfide.

4. A process of claim 3 wherein said mixture is devoid of any added liquid diluent.

5. A process of claim 3 wherein said mixture includes added inert liquid diluent.

6. A process of claim 3 wherein said mixture is heated to one or more temperatures in the range of about 40° to about 110° C.

7. A process of claim 3 wherein said mixture contains from about 0.3 to about 1.5 gram atoms of sulfur per gram mol of the mercaptan.

8. A process of claim 3 wherein said mixture is heated to one or more temperatures in the range of about 40° to about 110° C., wherein said mixture contains from about 0.3 to about 1.5 gram atoms of sulfur per gram mol of the mercaptan, and wherein said mixture contains about 0.005 to about 0.05 gram mol of alumina catalyst per gram mol of mercaptan charged thereto.

9. A process which comprises reacting tert-alkyl mercaptan with sulfur in the presence of a catalytically active form of added alumina catalyst in proportions and at a temperature which are sufficient to form a product enriched in di-tert-alkyl trisulfide wherein said temperature is about 25° C. to about 110° C.

10. A process as claimed in claim 9 wherein said tert-alkyl mercaptan is tert-butyl mercaptan.

11. A process as claimed in claim 9 wherein at least a substantial portion of said reaction is performed at a temperature within the range of about 60° to about 80° C.

12. A process as claimed in claim 9 wherein at least a substantial portion of said reaction is performed by heating in a reaction vessel a mixture consisting essentially of the mercaptan, sulfur and alumina catalyst, the aforesaid components of said mixture being fed to said vessel in proportions such that for every gram mol of the mercaptan there are from about 0.3 to about 1.5 gram atoms of sulfur, and for every gram mol of mercaptan there is from 0.005 to about 0.05 gram mol of alumina catalyst.

13. A process as claimed in claim 12 wherein said tert-alkyl mercaptan is tert-butyl mercaptan.

14. A process as claimed in claim 12 wherein the alumina catalyst is in particulate form.

15. A process as claimed in claim 12 wherein said reaction is conducted in bulk.

16. A process as claimed in claim 12 wherein said reaction is conducted in the presence of an inert liquid diluent.

17. A process as claimed in claim 12 wherein said tert-alkyl mercaptan is tert-butyl mercaptan, and wherein the alumina catalyst is an activated alumina in particulate form.

18. A process as claimed in claim 17 wherein the alumina catalyst is a neutral activated alumina in particulate form of about 80 to about 200 mesh size.

19. A process as claimed in claim 12 wherein said tert-alkyl mercaptan is tert-dodecyl mercaptan, and wherein the alumina catalyst is an activated alumina in particulate form.

20. A process as claimed in claim 9 wherein said tert-alkyl mercaptan is tert-nonyl mercaptan or tert-dodecyl mercaptan.

21. A process as claimed in claim 1 wherein the mercaptan is a primary hydrocarbyl mercaptan and the reaction conditions are controlled such that the product is enriched in dihydrocarbyl disulfide.

22. A process as claimed in claim 1 wherein the mercaptan is a primary hydrocarbyl mercaptan and the reaction conditions are controlled such that the product is enriched in dihydrocarbyl trisulfide.

23. A process as claimed in claim 1 wherein the mercaptan is a tertiary hydrocarbyl mercaptan and the reaction conditions are controlled such that the product is enriched in dihydrocarbyl trisulfide.

* * * * *